US006471974B1

(12) United States Patent
Rees et al.

(10) Patent No.: US 6,471,974 B1
(45) Date of Patent: Oct. 29, 2002

(54) N-CHLOROSULFAMATE COMPOSITIONS HAVING ENHANCED ANTIMICROBIAL EFFICACY

(75) Inventors: Wayne M. Rees, Caledonia; Debra S. Hilgers, Racine, both of WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 0 days.

(21) Appl. No.: 09/343,660

(22) Filed: Jun. 29, 1999

(51) Int. Cl.[7] .................... A01N 25/00; A61K 33/14; A61K 33/04

(52) U.S. Cl. .................. 424/405; 424/661; 424/665; 424/703; 252/187.25; 514/389

(58) Field of Search ................. 424/661, 665, 424/703, 405; 252/187.25; 514/389

(56) References Cited

U.S. PATENT DOCUMENTS

| | | | |
|---|---|---|---|
| 2,438,781 A | 3/1948 | Kamlet ................ 23/86 |
| 3,170,883 A | 2/1965 | Owen et al. ............ 252/187 |
| 3,177,111 A | 4/1965 | Larsen ................ 162/73 |
| 3,328,294 A | 6/1967 | Self et al. ............. 210/62 |
| 3,583,922 A | 6/1971 | McClain et al. ......... 252/99 |
| 3,749,672 A | * 7/1973 | Golton et al. .......... 252/186.34 |
| 3,767,586 A | 10/1973 | Rutkiewic ............. 252/187 H |
| 4,690,770 A | 9/1987 | Jeschke et al. ......... 252/99 |
| 4,729,845 A | 3/1988 | Altenschoepfer et al. .. 252/99 |
| 4,828,745 A | 5/1989 | Jeschke et al. ......... 252/99 |
| 4,913,832 A | 4/1990 | Kruse et al. ........... 252/99 |
| 4,992,209 A | 2/1991 | Smyk et al. ............ 252/387 |
| 5,064,554 A | 11/1991 | Jacobs et al. .......... 252/99 |
| 5,565,109 A | * 10/1996 | Sweeny ................. 210/755 |
| 5,683,654 A | 11/1997 | Dallmier et al. ........ 422/14 |
| 5,795,487 A | 8/1998 | Dallmier et al. ........ 210/754 |

FOREIGN PATENT DOCUMENTS

WO 96/27651 9/1996

OTHER PUBLICATIONS

Efficacy Data Requirements, "Sanitizer Test (for inanimate, non–food contact surfaces)", Proposed method prepared by Registration Division, Office of Pesticide Programs, EPA, one page, 1976.

Delaney, et al, "Bactericidal Properties of Chlorsulfamates", Journal of the Sanitary Engineering Division, Proceedings of the American Society of Civil Engineers, pp. 23–36, 1972.

Stuart, et al., "Swimming Pool Chlorine Stabilizers", Soap and Chemical Specialties, pp. 79–82, 112–113, 1964.

Ortenzio, et al., "A Standard Test for Efficacy of Germicides and Acceptability of Residual Disinfecting Activity in Swimming Pool Water", Journal of the A.O.A.C., vol. 47, No. 3, pp. 540–547, 1964.

U.S. Environmental Protection Agency, Sanitizer Test (for inanimate, non–food contact surfaces), D15/TSS–10, Jan. 7, 1982.

J.E. Delaney, et al., "Bactericidal Properties of Chlorsulfamates," Journal of the Sanitary Engineering Division—Proceedings of the American Society of Civil Engineers, Feb., 1972, p. 23–36.

L.S. Stuart, et al., "Swimming Pool Chlorine Stabilizers," Soap and Chemical Specialties, Aug., 1964, p. 79–113.

L.F. Ortenzio, et al., "A Standard Test for Efficacy of Germicides and Acceptability of Residual Disinfecting Activity in Swimming Pool Water," Journal of the A.O.A.C., vol. 47, No. 3, 1964, p. 540–547.

* cited by examiner

*Primary Examiner*—Russell Travers
*Assistant Examiner*—Shengjun Wang

(57) ABSTRACT

The antimicrobial efficacy of N-chlorosulfamate solutions, namely buffered aqueous combinations of $HClNSO_3^-$ (mono-N-chlorosulfamate) and $Cl_2NSO_3$ (di-N-chlorosulfamate), herein referred to as "stabilized hypochlorite", can be markedly enhanced by the addition of certain organic dopants. The dopants themselves are select hypochlorite stabilizing agents, which are known to readily form stable organochloramides when reacted with "free" hypochlorite (HOCl or NaOCl). Highly effective antimicrobial enhancing dopants include 5,5-dialkyl hydantoins, arylsulfonamides, and succinimides. Examples of these include 5,5-dimethylhydantoin, benzenesulfonamide, and succinimide. Other, less effective dopants include glycolurils. Generally, the dopant is present in a minor mole fraction, relative to the molar amount of stabilized hypochlorite present in the enhanced antimicrobial solution.

20 Claims, No Drawings

N-CHLOROSULFAMATE COMPOSITIONS HAVING ENHANCED ANTIMICROBIAL EFFICACY

BACKGROUND OF THE INVENTION

1. Field of the Invention

This invention relates to antimicrobial cleaning solutions, and to methods of making and using such solutions. In more detail, this invention relates to N-chlorosulfamate compositions having enhanced antimicrobial efficacy, and to methods of making and using such compositions.

2. Related Background Art

Although hypochlorite and hypochlorous acid solutions are highly effective antimicrobial agents, they also are highly reactive, chemically aggressive, and unstable solutions. As such, they are not good candidates for inclusion in antimicrobial cleaning solutions. Consequently, efforts have been made to develop more stable and user-friendly forms of hypochlorite and/or hypochlorous acid solutions. Generally, this has been accomplished by the generation of various N-chloro compounds (herein also referred to as stabilized hypochlorite solutions or stabilized hypochlorite species), by reaction of hypochlorite sources with various amines and amides. By the term "stable" or "stabilized" we mean a compound, solution or species in which the active ingredient does not degrade over a substantial period of time.

For example, U.S. Pat. No. 2,438,781 discloses a process for stabilizing alkali-metal hypochlorite solutions by the addition of a stabilizing agent such as benzene sulfonamide, benzene N-sodium sulfonamide or p-toluene sulfonamide. That patent also notes that the use of the disclosed stabilizing agents increases the germicidal activity of the hypochlorite solutions to which they are added.

Aqueous stabilized hypochlorite solutions, such as N-chlorosulfamate solutions, are also known. For example, U.S. Pat. No. 3,170,883 teaches the stabilization of chlorine solutions (e.g., yielding the hypochlorite ion) with the sulfamate ion in concentrations as low as 0.4 ppm with total available chlorine sufficient to give a free available chlorine in a lethal range of 0.2 ppm and more. The created stabilized chlorine solution is recommended for use in cooling towers. In addition, U.S. Pat. No. 3,177,111 teaches a process of bleaching cellulosic materials, particularly wood pulps, with an agent such as N-chlorosulfamic acid and N,N-dichlorosulfamic acid derived from an inorganic hypochlorite and sulfamic acid. The use of sulfamic acid with hypochlorite is said to reduce the amount of hypochlorite required to attain a predetermined level of bleaching by 40–80% of that otherwise required. It also allows the bleaching operation to be carried out at a pH substantially lower than normal and yields a pulp of materially higher viscosity and strength. U.S. Pat. No. 3,749,672 teaches a method of making stable aqueous systems of N-halo compounds, in which the N-halo compounds are formed by mixing an N-hydrogen compound (e.g., sulfamic acid, sulfamide, dimethylhydantoin) with NaOCl or NaOBr. The aqueous system is stabilized by including a buffer that maintains the pH of the system between 4 and 11. U.S. Pat. No. 3,767,586 similarly concerns a process of preparing stable solutions of N-halo compounds by reaction of an N-hydrogen compound, preferably sulfamic acid, in the presence of hydroxides.

Stabilized hypochlorite solutions such as N-chlorosulfamate solutions are also known to possess antimicrobial activity. For example, in U.S. Pat. Nos. 3,749, 672 and 3,767,586, the processes are said to produce solutions that are useful for bleaching and for controlling microorganisms in process streams. Furthermore, U.S. Pat. No. 3,328,294 discusses the preparation and use of N-chlorosulfamate solutions to control microbial organisms in aqueous process streams.

N-chlorosulfamate solutions, however, have not been considered highly desirable as biocidal or disinfecting agents in areas of human contact, for example, in swimming pools, which require rapid microbial elimination. This is due to their weak antimicrobial activity relative to other hypochlorite-containing compounds such as NaOCl, HOCl, chlorinated isocyanuric acids (e.g., trichloroisocyanuric acid and sodium dichloroisocyanurate), and chlorinated hydantoins (e.g., 1,3-dichloro-5,5-dimethylhydantoin). (See, for example: J. E. Delaney and J. C. Morris, *Bactericidal Properties of Chlorosulfamates,* Journal of the Sanitary Engineering Division-Proceedings of the American Society of Civil Engineers, 98 (SA1), 23–36; L. S. Stuart and L. F. Ortenzio, *Swimming Pool Chlorine Stabilizers,* Soap and Chemical Specialties, August (1964); and L. F. Ortenzio and L. S. Stuart, *A Standard Test for Efficacy of Germicides and Acceptability of Residual Disinfecting Activity in Swimming Pool Water,* Journal of the A.O.A.C., 47, 540–547 (1964).) This is unfortunate because N-chlorosulfamate solutions not only are highly stable, but also have a pH that is near the neutral range. Solutions having a pH near the neutral range are highly desirable due to their reduced tendency to cause human irritation and property damage when used.

Finally, U.S. Pat. No. 5,565,109 teaches that certain N-hydrogen compounds (e.g., dimethylhydantoin, methylhydantoin, cyanuric acid, succinimide, and glycoluril) and their chlorinated derivatives can dramatically improve the bactericidal efficacy of hypochlorite solutions in pulp slurries, presumably by increasing the lifespan of the active chlorine. According to the '109 patent, the addition of dimethylhydantoin to sodium hypochlorite solutions enhances the biocidal activity of sodium hypochlorite, and the activity of hydantoins are greater than sulfamic acid and similar to cyanuric acid.

However, hypochlorite solutions stabilized with sulfamic acid or sulfamate exhibit superior long-term chemical stability in comparison to hypochlorite solutions stabilized with 5,5-dialkyl hydantoin or isocyanuric acid derived compounds. In addition, stabilized hypochlorite solutions containing alkyl hydantoin or cyanuric acid compounds usually are formulated as a suspension or slurry due to the lack of the solubility of the named N-chloro compounds in the hypochlorite-containing composition. In contrast, stabilized hypochlorite solutions containing sulfamic acid typically remain as a homogeneous (single-phase) solution. Homogeneous (single-phase) solutions are preferred by consumers and thus are more commercially viable.

Consequently, there is a need for an enhanced antimicrobial solution that can be used in various applications, including household cleaners, process streams and cooling towers. In particular, it would be useful to have a highly effective antimicrobial solution that not only is a stable, ready-to-use solution that does not give off annoying chlorine fumes, but also is a solution that is "user friendly" due to its mildly acid to near-neutral pH.

SUMMARY OF THE INVENTION

Surprisingly, we have found that hypochlorite solutions stabilized by the addition of sulfamate and additionally containing certain organoamide dopants possess enhanced antimicrobial activity relative to the initial sulfamate-only stabilized hypochlorite solution. This is an unexpected result due to the known lack of antimicrobial effectiveness of hypochlorite solutions stabilized with sulfamate.

Specifically, in one aspect, we have invented an antimicrobial solution comprising: a stabilized hypochlorite solution consisting essentially of a buffered aqueous combination of mono-N-chlorosulfamate ($HClNSO_3^-$) and di-N-chlorosulfamate ($Cl_2NSO_3^-$); and at least a dopant selected from the group consisting of a dialkyl hydantoin, preferably 5,5-dialkyl hydantoins, (e.g., 5,5-dimethylhydantoin, 5-ethyl-5-methylhydantoin, or 5,5-diethylhydantoin), an aryl sulfonamide (e.g., benzene sulfonamide, toluene sulfonamide, 4-carboxybenzensulfonamide), a succinimide and a glycoluril. The stabilized hypochlorite solution enhanced with a dopant has a pH between about 2 and about 10, preferably between about 2 and about 7, and most preferably between about 3 and about 6.

In another aspect, our invention also provides a stabilized hypochlorite solution having enhanced antimicrobial properties comprising: a hypochlorite stabilized by sulfamate; and a dopant selected from the group consisting of 5,5-dialkyl hydantoins, aryl sulfonamides, succinimides and glycolurils.

In yet another aspect, our invention further provides a stabilized hypochlorite composition having enhanced microbial efficacy, and having a sulfamate to hypochlorite mole ratio of at least about 0.5:1.0, and a minimum mole ratio of dopant to hypochlorite of about 1:50. The concentration of total available chlorine present is preferably about 10 to about 100,000 parts per million, more preferably, about 100 to about 50,000 parts per million.

Additionally, our invention provides a method of making an enhanced antimicrobial solution, comprising: (a) forming a stabilized hypochlorite solution by adding a source of hypochlorite to a buffered source of sulfamate; and (b) adding at least one dopant selected from the group consisting of dialkyl hydantoins such as 5,5-dialkyl hydantoins, aryl sulfonamides, succinimides and glycolurils to the stabilized hypochlorite solution formed in step (a) to form an enhanced antimicrobial solution, such that the mole ratio of dopant to hypochlorite is at least about 1:50, and the sulfamate to hypochlorite mole ratio is at least about 0.5:1.0.

In an alternative embodiment, we provide a method of making an enhanced antimicrobial solution, comprising: (a) forming a stabilized hypochlorite solution by adding a source of hypochlorite to a buffered source of sulfamate; and (b) adding at least one chlorinated dopant selected from the group consisting of chlorinated dialkyl hydantoins such as chlorinated 5,5-dialkyl hydantoins, chlorinated aryl sulfonamides, chlorinated succinimides and chlorinated glycolurils to the stabilized hypochlorite solution formed in step (a) to form an enhanced antimicrobial solution, such that the mole ratio of dopant to hypochlorite is at least about 1:50, and the sulfamate to hypochlorite mole ratio is at least about 0.5:1.0. In this embodiment of the invention, the hypochlorite content of the composition arises from the hypochlorite sources in steps (a) and (b) above.

In yet another alternative embodiment, we provide a method of making an enhanced antimicrobial solution, comprising combining a buffered source of sulfamate with a source of hypochlorite, such that the mole ratio of sulfamate to hypochlorite is at least about 0.5:1.0, wherein the source of hypochlorite is comprised of at least one chlorinated dopant selected from the group consisting of chlorinated dialkyl hydantoins such as 5,5-dialkyl hydantoins, chlorinated aryl sulfonamides, chlorinated succinimides and chlorinated glycolurils.

In yet another embodiment, our invention provides a method of reducing a microbe population comprising the steps of: (a) applying to a surface a stabilized hypochlorite aqueous solution having a sulfamate to hypochlorite mole ratio of at least about 0.5:1.0, and a minimum mole ratio of dopant to hypochlorite of about 1:50, wherein the composition has a pH between about 2 and about 10, and the concentration of total available chlorine present is about 10 to about 100,000 parts per million; and (b) allowing the composition to remain in contact with the surface for a period sufficient to kill at least a major fraction of the microbe population on the surface.

In yet another embodiment, our invention provides a method of controlling a microbe population in, for example, a process stream or in a cooling tower, comprising the step of adding to the process stream or the cooling tower a stabilized hypochlorite aqueous solution having a sulfamate to hypochlorite mole ratio of at least about 0.5:1.0, and a minimum mole ratio of dopant to hypochlorite of about 1:50, wherein the composition has a pH between about 2 and about 10, and the concentration of total available chlorine present is about 10 to about 100,000 parts per million.

In each of the above embodiments, preferably the mole ratio of sulfamate to hypochlorite ratio is between about 0.5:1 and about 5:1. More preferably, in each of the above embodiments, the mole ratio of sulfamate to total hypochlorite is between about 0.7:1 and about 3:1. Most preferably, in each of the above embodiments, the mole ratio of sulfamate to total hypochlorite is between about 1:1 and about 2:1.

As well, in each of the above embodiments, preferably the mole ratio of dopant to hypochlorite is at least about 1:25. Most preferably, in each of the above embodiments, the mole ratio of dopant to hypochlorite is at least about 1:10.

DETAILED DESCRIPTION OF THE INVENTION

The antimicrobial efficacy of N-chlorosulfamate solutions, namely buffered aqueous combinations of $HClNSO_3^-$ (mono-N-chlorosulfamate) and $Cl_2NSO_3$ (di-N-chlorosulfamate), herein referred to as "stabilized hypochlorite", can be markedly enhanced by the addition of certain organic dopants (a.k.a. doping agents or enhancing agents). The term "hypochlorite" in "stabilized hypochlorite" generally refers to any form of chlorine in the +1 oxidation state (unipositive chlorine). The dopants themselves are select hypochlorite stabilizing agents, which are known to readily form stable organochloramines when reacted with "free" hypochlorite (HOCl or NaOCl). Highly effective antimicrobial enhancing dopants include dialkyl hydantoins (preferably 5,5-dialkyl hydantoins), arylsulfonamides, and succinimides. Examples of 5,5-dialkyl hydantoins include 5,5-dimethylhydantoin, 5-ethyl-5-methylhydantoin and 5,5-diethylhydantoin. Examples of aryl sulfonamides include benzene sulfonamide, toluene sulfonamide, 4-carboxybenzensulfonamide, and a substituted derivative of any one of these compounds. Various other substituted derivatives of the parent compounds mentioned above should be effective enhancing agents as well (for example, 4-ethylbenzenesulfonamide). Less effective dopants include glycolurils. To date, we have not found melamine or cyanuric acid to be performance enhancing dopants. The invention is unexpected, as one skilled in the art would not anticipate an additional stabilizing agent/ dopant to greatly enhance the antimicrobial efficacy of a stabilized hypochlorite (N-chlorosulfamate) composition.

It is preferred, but not required, that the dopant be present in a minor mole fraction, relative to the molar amount of hypochlorite present in the enhanced antimicrobial solution. The stabilized hypochlorite compositions having enhanced microbial efficacy can be chemically described as having a sulfamate to hypochlorite mole ratio of at least about 0.5:1.0 (for example, 1 mole of sulfamate to 1 mole of total hypochlorite) and a mole ratio of organic enhancer (dopant) to hypochlorite of at least about 1:50 (for example, 1 mole of 5,5-dimethylhydantoin to 30 moles of hypochlorite). Preferably, the mole ratio of sulfamate to hypochlorite ratio is between about 0.5:1 and about 5:1; more preferably, this mole ratio is between about 0.7:1 and about 3:1 most preferably, this mole ratio is between about 1:1 and about 2:1. Furthermore, preferably, the mole ratio of dopant to hypochlorite is at least about 1:25, (for example, 1 mole of benzenesulfonamide to 25 moles of total hypochlorite). Most preferably, the mole ratio of dopant to hypochlorite is at least about 1:10 (for example, 1 mole of dimethylhydantoin to 10 moles of total hypochlorite).

The concentration of total available chlorine present in these stabilized hypochlorite solutions having enhanced antimicrobial efficacy is preferably about 10 to 100,000 ppm, more preferably in the range of about 100 to 50,000 ppm. The terms "total available chlorine (TAC)" and "free available chlorine (FAC)" concentrations are expressed in the conventional terms of mg $Cl_2$ per kg of solution (ppm $Cl_2$).

The stabilized hypochlorite composition of this invention is prepared from a source of unipositive chlorine ion. A convenient source of this ion is an inorganic hypochlorite salt. Other convenient sources of unipositive chlorine ions include, for example, hypochlorous acid and aqueous solutions of chlorine gas, and N-chloro compounds. The inorganic hypochlorite salts employed in the present invention include, for example, potassium hypochlorite, sodium hypochlorite, lithium hypochlorite and calcium hypochlorite. Examples of N-chloro compounds include 1,3-dichloro-5,5-dimethylhydantoin, N-chlorosuccinimide, and N-chloro-N-sodiobenzene-sulfonamidate. Generally, the hypochlorite source is utilized in an amount between about 0.001% to about 10% by weight of the composition, preferably between about 0.01% to about 5% by weight of the composition.

It should also be noted that a chlorinated dopant, such as, for example, chlorinated dialkyl hydantoin, chlorinated aryl sulfonamide, chlorinated succinimide and chlorinated glycoluril, could conceivably also be used as a source of hypochlorite.

The pH of the stabilized hypochlorite solution having enhanced antimicrobial efficacy should be in the range of about pH 2 to about pH 10, preferably in the range of about pH 2 to about pH 7, and most preferably in the range of about pH 3 to about pH 6.

We have found that the invention is best practiced in the form of a buffered aqueous solution. These solutions should be buffered with a suitable, inert buffer. A preferable, inert buffering system is an acidic system, comprising a weak acid ($pK_a$ from about 2 to about 7) and its conjugate base, and capable of stabilizing the pH in the range from about 2 to about 6.5. Examples of suitable buffers include those derived from citric acid, succinic acid, glutaric acid, adipic acid, acetic acid, propanoic acid, polyacrylic acid, phosphoric acid, boric acid, copolymers of maleic acid with vinyl ethers, copolymers of acrylic acid with maleic acid, and copolymers of acrylic acid with vinyl ethers. By buffers "derived" from an acid, we mean that the buffer is prepared by combining that acid with its conjugate base to form a homogenous system. Preferred buffer systems are those based on citric acid and polyacrylic acid. The buffer system is present in an amount ranging from about 0.1% to about 20% by weight of the composition, preferably from about 0.5% to about 10% by weight of the composition. Buffers that are inherently unstable to oxidation, such as those derived from lactic acid and malic acid, which have a secondary hydroxyl group making them highly susceptible to oxidation by an active chlorine source, should not be used.

The composition of this invention contains water as the solvent due to its low cost and environmental and safety concerns. However, if desired, other solvents may be admixed. Such exemplary solvents include tertiary alcohols, e.g., tert-butyl alcohol and tert-amyl alcohol, as well as various glymes and polyglymes (e.g., dialkyl ethers of ethylene glycol, diethylene glycol, propylene glycol, and dipropylene glycol), which can enhance the cleaning of oil-borne stains.

The solutions of this invention may also contain other ingredients such as surfactants, chelating agents, fragrances, bromide ion containing salts, sources of hypobromite, and thickeners. Many of the buffers noted earlier can also be used as chelating agents (e.g., citrate or acrylate).

Surfactant(s) may be included to enhance the cleaning and/or foaming properties of the inventive composition. Such surfactants include, but are not limited to, anionic sulfonated or sulfated surfactants, for example, linear alkyl benzene sulfonates, alkyl sulfates, alkyl sulfonates, alcohol ether sulfates, and the like. Preferred surfactants are sodium lauryl sulfate, sodium dodecylbenzenesulfonate, secondary alkyl sulfonates, sodium lauryl ether sulfates, alcohol ethoxy carboxylates and alkyl diphenyl oxide disulfonates. Other surfactants that may be present, but are less preferred, are ethoxylated nonionic surfactants, amine oxides, e.g., lauryl dimethyl amine oxide, alkyl betaines, alkyl sulfobetaines, and tetraalkyl quaternary ammonium surfactants. The amount of surfactant utilized in the inventive composition is determined by the surfactant cleaning properties as well as the particular application for which the acidic bleaching composition is formulated. Generally, the surfactant is present in an amount between about 0.05% and about 10% by weight of the composition, preferably between about 0.1% and about 5% by weight of the composition.

A source of unipositive bromine ion is optionally added to the composition of this invention to further enhance bleaching and microbial control performance. Elemental bromine, or a bromide or bromate salt of lithium, sodium, potassium, calcium, magnesium, or zinc, in combination with the source of unipositive chlorine ion may serve as a source of unipositive bromine ion. Inorganic hypobromite salts, such as NaOBr, also can be added directly. Stabilized hypobromite compounds such as brominated hydantoins, succinimides, arene sulfonamides, isocyanuric acids, and glycolurils may also be employed as the source of hypobromite. Examples include N-bromo-succinimide, 1,3-dibromo-5,5-dimethylhydantoin, and N-bromo-N-sodiobenzene sulfonamidate. The source of unipositive bromine ion may be present in amounts ranging from about 0.01% to about 5%, preferably from about 0.05% to about 2%.

The compositions of this invention may also contain thickening agents to enhance the viscosity of the compositions. Increasing the viscosity of the compositions can improve their optimal use on vertical surfaces. Such thickened compositions generally would have a viscosity in a range from about 10 centipoise to about 3500 centipoise at about room temperature, preferably about 100 centipoise to about 2500 centipoise, and most preferably about 100 centipoise to 1000 centipoise. Exemplary thickening agents include surfactants such as alkyl ether sulfates, oxidation resistant polymers such as acrylate resins (e.g., Carbopol® 672 or 676, B.F. Goodrich Specialty Chemicals, Cleveland, Ohio), or clays (e.g., Laponite®, Southern Clay Products, Inc., Gonzales, Tex.).

In preparing our antimicrobial solution, we prefer sulfamic acid as a source of sulfamate, whereas the preferred source of hypochlorite is sodium hypochlorite. However, it should be noted that, if our enhanced antimicrobial solution is made using a chlorinated dopant (e.g., such as chlorinated 5,5-dialkyl hydantoin, chlorinated aryl sulfonamide, chlorinated succinimide or chlorinated glycoluril), the chlorinated dopant could function as a source of some or all of the hypochlorite.

Surfactants, chelating agents, fragrances, bromide-ion containing salts, hypobromite sources and thickeners, as described earlier, can be added to the enhanced antimicrobial solution.

The enhanced antimicrobial solution of the present invention can be made in a number of ways. For example, the enhanced antimicrobial solution can be made by a method comprising:(a) forming a stabilized hypochlorite solution by adding a source of hypochlorite to a buffered source of sulfamate; and (b) adding at least one dopant selected from the group consisting of dialkyl hydantoins (e.g., 5,5-dialkyl hydantoin), aryl sulfonamides, succinimides and glycolurils to the stabilized hypochlorite solution formed in step (a) to form an enhanced antimicrobial solution, such that the minimum mole ratio of dopant to hypochlorite is about 1:50, and the sulfamate to hypochlorite ratio is at least about 0.5:1.0.

Alternatively, the enhanced antimicrobial solution can be made by a method comprising:(a) forming a stabilized hypochlorite solution by adding a source of hypochlorite to a buffered source of sulfamate; and (b) adding at least one chlorinated dopant selected from the group consisting of chlorinated dialkyl hydantoins (e.g., chlorinated 5,5-dialkyl hydantoins such as 1,3-dichloro-5,5-dimethylhydantoin, 1,3-dichloro-5-ethyl-5-methylhydantoin and 1,3-dichloro-5,5-diethylhydantoin), chlorinated aryl sulfonamides (e.g., N-chloro aryl sulfonamide, N,N-dichloro aryl sulfonamide, or a salt of a chlorinated aryl sulfonamide), chlorinated succinimides (e.g., N-chlorosuccinimide) and chlorinated glycolurils to the stabilized hypochlorite solution formed in step (a) to form an enhanced antimicrobial solution, such that the mole ratio of dopant to hypochlorite is at least about 1:50, and the sulfamate to hypochlorite mole ratio is at least about 0.5:1.0. As noted previously, in this process of making the enhanced anti-microbial solution, the hypochlorite content of the composition arises from the hypochlorite sources in steps (a) and (b) above.

In either of these methods, preferably the mole ratio of sulfamate to hypochlorite is between about 0.5:1 and about 5:1; more preferably, this mole ratio is between about 0.7:1 and about 3:1; most preferably, this mole ratio is between about 1:1 and about 2:1. Furthermore, in either method, preferably, the mole ratio of dopant to hypochlorite is at least about 1:25; most preferably, the mole ratio of dopant to hypochlorite is at least about 1:10.

The enhanced antimicrobial solution can also be made by a method comprising combining a buffered source of sulfamate with a source of hypochlorite, such that the mole ratio of sulfamate to hypochlorite is at least about 0.5:1.0, wherein the source of hypochlorite is comprised of at least one chlorinated dopant selected from the group consisting of chlorinated dialkyl hydantoins (e.g., chlorinated 5,5-dialkyl hydantoins such as 1,3-dichloro-5,5-dimethylhydantoin, 1,3-dichloro-5-ethyl-5-methyl-hydantoin and 1,3-dichloro-5,5-diethylhydantoin), chlorinated aryl sulfonamides (e.g., N-chloro aryl sulfonamide, N,N-dichloro aryl sulfonamide, or a salt of a chlorinated aryl sulfonamide), chlorinated succinimides (e.g., N-chlorosuccinimide) and chlorinated glycolurils. In this method, the mole ratio of hypochlorite to dopant is dictated by the selection of the chlorinated dopant or dopants. Preferably, the mole ratio of sulfamate to hypochlorite is between about 0.5:1 and about 5:1; more preferably, this mole ratio is between about 0.7:1 and about 3:1; most preferably, this mole ratio is between about 1:1 and about 2:1.

Any of the above three methods of making the enhanced antimicrobial solution can further comprise a step of diluting the enhanced antimicrobial solution with water prior to use.

Using any of the above three methods, the enhanced antimicrobial solution ultimately produced has a buffered pH between about 2 and about 10, preferably between about 2 and about 7, and most preferably between about 3 and about 6. Furthermore, the concentration of total available chlorine present in the enhanced antimicrobial solution should preferably be between about 10 to about 100,000 parts per million, more preferably between about 100 to about 50,000 parts per million.

As an example of the type of reactions that might generate a stabilized hypochlorite solution, sodium hypochlorite and sulfamic acid (i.e., a source of sulfamate ion) can react in various steps to form N-mono and N,N-dichlorosulfamate salts thereof. The chemical reaction between sulfamic acid and hypochlorite in a buffered aqueous solution may be represented by the following chemical equations:

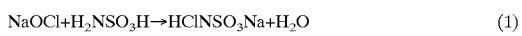
$$NaOCl + H_2NSO_3H \rightarrow HClNSO_3Na + H_2O \qquad (1)$$

$$NaOCl + HClNSO_3Na + H^+ \rightarrow Cl_2NSO_3^-Na + H_2O + Na^+ \qquad (2)$$

$$2NaOCl + H_2NSO_3H + H^+ \rightarrow Cl_2NSO_3^-Na + 2H_2O + Na^+ \qquad (3)$$

The stabilized hypochlorite solution of our invention comprises buffered aqueous combinations of mono-N-chlorosulfamate ($HClNSO_3^-$) and di-N-chlorosulfamate ($Cl_2NSO_3^-$) that can, for example, be generated by the reactions described above.

Optionally, a source of hypochlorite may also be the chlorinated dopant, such as chlorinated 5,5-dialkyl hydantoin, chlorinated aryl sulfonamide, chlorinated succinimide and chlorinated glycoluril. Examples of chlorinated dopants include N-chlorosuccinimide ($ClNC_4H_4O_2$), 1,3-dichloro-5,5-dimethylhydantoin, and chloramine-T (N-chloro-N-sodiotoluenesulfonamidate).

In these compositions, it is believed that an exchange of unipositive chlorine takes place such that, at equilibrium, the solution largely consists of mono-N-chlorosulfamate, di-N-chlorosulfamate, non-chlorinated dopant (for example, succinimide, $HNC_4H_4O_2$), along with small amounts of the chlorinated dopant (for example, N-chlorosuccinimide, $ClNC_4H_4O_2$). Enhancements in antimicrobial activity are thought to arise from the small equilibrium concentrations of chlorinated dopants in the buffered N-chloro-sulfamate solutions.

In yet another embodiment, we provide a method of reducing a microbe population comprising the steps of:(a)

applying to a surface a stabilized hypochlorite aqueous solution having a sulfamate to hypochlorite mole ratio of at least about 0.5:1.0, and a minimum mole ratio of dopant to hypochlorite of about 1:50, wherein the composition has a pH between about 2 and about 10, preferably between about 2 and about 7, and most preferably between about 3 and about 6, and the concentration of total available chlorine present is about 10 to about 100,000 parts per million; and (b) allowing the composition to remain in contact with the surface for a period sufficient to kill at least a major fraction of the microbe population on the surface. Preferably, the composition can be allowed to remain in contact with the surface for a period sufficient to kill at least about 90% of the microbe population on the surface. Also, preferably, the stabilized hypochlorite aqueous solution can be applied to a hard or soft surface.

The antimicrobial solution of the present invention can also be used in, for example, process streams and/or cooling towers, as a method of microbial control. That is, another embodiment of this invention is directed to a method of controlling a microbe population in a process stream or cooling tower, comprising the step of adding to the process stream a stabilized hypochlorite aqueous solution having a sulfamate to hypochlorite mole ratio of at least about 0.5:1.0, and a minimum mole ratio of dopant to hypochlorite of about 1:50, wherein the composition has a pH between about 2 and about 10 preferably between about 2 and about 7, and most preferably between about 3 and about 6, and wherein the concentration of total available chlorine present is about 10 to about 100,000 parts per million.

In the embodiments set out above, preferably the mole ratio of sulfamate to hypochlorite ratio is between about 0.5:1 and about 5:1; more preferably, this mole ratio is between about 0.7:1 and about 3:1; most preferably, this mole ratio is between about 1:1 and about 2:1. Furthermore, preferably, the mole ratio of dopant to hypochlorite is at least about 1:25; most preferably, the mole ratio of dopant to hypochlorite is at least about 1:10.

The invention described herein is useful for a variety of cleaning applications where antimicrobial properties are desired. This includes "ready-to-use" cleaner applications, as well as compositions intended for dilution with additional water prior to use.

EXAMPLES

Examples of antimicrobial enhancement are provided below to demonstrate the improved performance of the modified (doped) stabilized hypochlorite compositions of the present invention.

Example 1

Materials and Methods

The test method used to evaluate antimicrobial efficacy was the Sanitizer Test described below. This Sanitizer Test parallels the U.S. Environmental Protection Agency (EPA) Non-Food Contact Sanitizer Test, DIS/TSS-10 (Jan. 7, 1982), the content of which is incorporated herein by reference.

Sanitizer Test: Glass slides measuring 18×36 mm were washed in a dishwasher, placed in glass petri dishes on 2 pieces of Whatman no. 2 filter paper and autoclaved. The slides were inoculated with a 10 μl sterile bacterial loop. The inoculum was spread over the upper surface of the slide being careful not to exceed the edges of the slide. The inoculum was a 24 hour culture having a concentration of approximately $10^9$ organisms per ml. Following inoculation, the slides were incubated at 35° C. for 30±5 minutes to allow the slides to dry. The test product was then sprayed liberally onto the test surface (6 sprays/slide—approximately 6 ml of product) and the slides were allowed to stand for the desired contact time. The slides were removed from the petri dish using flamed forceps after exposure to the test product for the specified contact time and placed into test tubes containing 15.0 ml of the desired neutralizer for neutralization of the test product. Both 2× Letheen Broth (Tween 80 & Lecithin) and Dey/Engley neutralizing broths were separately utilized. Test bacteria was recovered by vortexing each test tube for 15 seconds. Serial dilutions were made using diluent. The pour plate technique using Tryptic Soy Agar was used to obtain plate counts. Parallel tests were run using a citrate-buffered (pH 5) solution of the dopant at a concentration equal to that in the doped test solutions or a 0.01% solution of Triton X-100 (isooctylphenoxy-polyethoxyethanol with 9–10 moles oxyethylene) in an identical manner to serve as controls. Blank parallel controls, using sterile, de-ionized water as the test product, were also evaluated.

A 5-minute contact time using a glass slide test surface was employed. *Staphylococcus aureus* (ATCC 25923) was the inoculum/test organism used in the antimicrobial activity evaluations.

The following test products were used:

Base Stabilized Hypochlorite Composition # 1: 985 ppm total available chlorine (TAC), 1.0 to 1.0 mole ratio of sulfamate to NaOCl used to prepare the solution, pH 5 citric acid buffer (0.25%), free available chlorine (FAC) determined as 155 ppm.

Base Stabilized Hypochlorite Composition #2: 2010 ppm total available chlorine (TAC), 1.0 to 1.0 mole ratio of sulfamate to NaOCl used to prepare the solution, pH 5 citric acid buffer (0.5%), free available chlorine (FAC) determined as 300 ppm.

Dopant (Doped Solutions): The following compounds were added to Base Stabilized Hypochlorite Composition 1 at a mole ratio of dopant to hypochlorite of 0.20 to 1.0; 5,5-dimethylhydantoin, benzenesulfonamide, 4-carboxybenzenesulfonamide, toluenesulfonamide, and succinimide.

Control Solutions: pH 5 citric acid buffer (0.25%), also containing the compounds used above as dopants at concentrations equal to those in the doped solutions.

Results

Results, expressed as "log reductions", are reported in comparison to the blank parallel controls. Thus, a "3 log reduction" means that 99.9% of the organism has been killed, whereas a "5 log reduction" means that 99.999% of the organism has been killed, relative to the number of organisms recovered from the blank parallel control.

| Test Solution | Dopant | Log Reduction | FAC/TAC |
|---|---|---|---|
| Base Composition 1 | None | 2–3 | 155/985 |
| Base Composition 2 | None | 3–4 | 300/2010 |
| Doped Solution 1 | 5,5-Dimethylhydantoin | ≧5 | 175/985 |
| Doped Solution 2 | Benzensulfonamide | ≧5 | 165/985 |
| Doped Solution 3 | Toluenesulfonamide | ≧5 | 155/985 |
| Doped Solution 4 | 4-Carboxybenzenesulfonamide | ≧5 | 145/985 |
| Doped Solution 5 | Succinimide | ≧5 | 155/985 |
| Control Solution 1 | 5,5-Dimethylhydantoin | <2 | 0 |
| Control Solution 2 | Benzenesulfonamide | <2 | 0 |
| Control Solution 3 | Toluenesulfonamide | <2 | 0 |
| Control Solution 4 | Succinimide | <2 | 0 |

Conclusions

Thus, it can be seen that the addition of dimethylhydantoin, benzenesulfonamide, toluenesulfonamide, 4-carboxybenzenesulfonamide or succinimide to the Base Stabilized Hypochlorite Composition 1 as a dopant significantly enhances the antimicrobial activity of the base composition. Notably, the doped stabilized hypochlorite compositions show antimicrobial activity markedly greater than that of Base Stabilized Hypochlorite Composition 2, which has twice the FAC and TAC concentrations of the doped solutions. In addition, the control solutions show that the dopant and pH 5 citric acid buffer by themselves do not contribute to the antimicrobial efficacy of the compositions.

Example 2

Materials and Methods

The same method as in Example 1 was used in Example 2. The test products used are described below.

Base Stabilized Hypochlorite Composition # 3: 985 ppm total available chlorine (TAC), 1.0 to 1.0 mole ratio of sulfamate to NaOCl used to prepare solution, pH 5 citric acid buffer (0.25%), free available chlorine (FAC) determined as 150 ppm.

Base Stabilized Hypochlorite Composition # 2: 1985 ppm total available chlorine (TAC), 1.0 to 1.0 mole ratio of sulfamate to NaOCl used to prepare solution, pH 5 citric acid buffer (0.5%), free available chlorine (FAC) determined as 310 ppm.

Dopant (Doped Solutions): The following compounds were added to Base Stabilized Hypochlorite Composition 1 at a mole ratio of dopant to hypochlorite of 0.20 to 1.0; melamine, cyanuric acid, toluenesulfonamide, and glycoluril.

Control Solutions: pH 5 citric acid buffer (0.25%), also containing the compounds used above as dopants at concentrations equal to those in the doped solutions.

Results

| Test Solution | Dopant | Log Reduction | FAC/TAC |
| --- | --- | --- | --- |
| Base Composition 3 | None | 2–3 | 155/985 |
| Base Composition 4 | None | 3–4 | 310/1985 |
| Doped Solution 6 | Toluenesulfonamide | ≧6 | 160/985 |
| Doped Solution 7 | Glycoluril | 3 | 175/985 |
| Doped Solution 8 | Cyanuric acid | 2–3 | 155/985 |
| Doped Solution 9 | Melamine | 2–3 | 177/985 |
| Control Solution 5 | Toluenesulfonamide | <2 | 0 |
| Control Solution 6 | Glycoluril | <2 | 0 |
| Control Solution 7 | Cyanuric acid | <2 | 0 |
| Control Solution 8 | Melamine | <2 | 0 |

Conclusions

Thus, the above results confirm the antimicrobial enhancing ability of toluenesulfonamide as a dopant, as seen in the Example 1 results. Glycoluril dopant appears to have a modest antimicrobial benefit, while cyanuric acid and melamine do not appear to have an antimicrobial enhancing effect.

Example 3

Additional Antimicrobial Data

Materials and Methods

The test method used to evaluate antimicrobial efficacy was, once again, the Sanitizer Test of Example 1 that parallels the U.S. EPA Non-Food Contact Sanitizer Test, DIS/TSS-10 (Jan. 7, 1982). However, a 1-minute contact time using a glass slide test surface was employed. *Staphylococcus aureus* was the test organism used. The test products that were used are described below.

Base Stabilized Hypochlorite Composition # 1: 500 ppm total available chlorine, 1.0 to 1.0 mole ratio of sulfamate to NaOCL, pH 5 citric acid buffer (0.13%). Composition also used to prepare doped solutions 1–3.

Base Stabilized Hypochlorite Composition # 2: 200 ppm total available chlorine, 1.0 to 1.0 mole ratio of sulfamate to NaOCl, pH 5 citric acid buffer (0.07%). Composition also used to prepare doped solution 4–6.

Dopant (Doped Solutions): The following compounds were added to a Base Stabilized Hypochlorite Composition at a mole ratio of dopant to hypochlorite of 0.20 to 1.0: 5,5-dimethylhydantoin, benzenesulfonamide and succinimide.

Results

Results are reported as a bacterial reduction (log reduction) of the formulation

| Test Solution | Dopant | Log Reduction |
| --- | --- | --- |
| Base Composition 1 | None | <3 |
| Doped Solution 1 | 5,5-Dimethylhydantoin | 3 |
| Doped Solution 2 | Benzenesulfonamide | >5 |
| Doped Solution 3 | Succinimide | >5 |
| Base Composition 2 | None | <3 |
| Doped Solution 4 | 5,5-Dimethylhydantoin | 3 |
| Doped Solution 5 | Benzenesulfonamide | >5 |
| Doped Solution 6 | Succinimide | 3–4 |

Conclusions

These test results confirm that stabilized hypochlorite solutions containing each of 5,5-dimethylhydantoin, benzenesulfonamide and succinimide, have antimicrobial effectiveness, even at lower total available chlorine levels. However, such solutions containing benzenesulfonamide are most effective, even at low levels (i.e., 200 ppm) of total available chlorine, followed by stabilized hypochlorite solutions containing succinimide. At lower levels of total available chlorine (i.e., 500 and 200 ppm), stabilized hypochlorite solutions containing dimethylhydantoin exhibited the lowest levels of enhanced antimicrobial efficacy.

Example 4

Additional Antimicrobial Data

Materials and Methods

The test method used to evaluate antimicrobial efficacy was, once again, the Sanitizer Test of Example 1 that parallels the U.S. EPA Non-Food Contact Sanitizer Test, DIS/TSS-10 (Jan. 7, 1982). However, a 1-minute contact time using a glass slide test surface was employed, and *Klebsiella pneumoniae* (ATCC 4352) was the inoculum/test organism used. The test products used are described below.

Base Stabilized Hypochlorite Composition # 1: 100 ppm total available chlorine, 1.0 to 1.0 mole ratio of sulfamate to NaOCl, pH 5 citric acid buffer (0.03%). Composition also used to prepare doped solutions 1–3.

Doped Solutions: The following compounds were added to the Base Stabilized Hypochlorite Composition at a mole ratio of dopant to hypochlorite of 0.20 to 1.0: 5,5-dimethylhydantoin, benzenesulfonamide and succinimide.

Control Solutions: pH 5 citric acid buffer (0.03%), also containing the compounds used above as dopants at concentrations equal to those in the doped solutions.

Results

Results are reported as a bacterial reduction (log reduction) of the formulation over a blank parallel control.

| Test Solution | Dopant | Log Reduction |
|---|---|---|
| Base Composition 1 | None | <3 |
| Doped Solution 1 | 5,5-Dimethylhydantoin | 5 |
| Doped Solution 2 | Benzenesulfonamide | >5 |
| Doped Solution 3 | Succinimide | >5 |
| Control Solution 1 | 5,5-Dimethylhydantoin | <2 |
| Control Solution 2 | Benzenesulfonamide | <2 |
| Control Solution 3 | Succinimide | <2 |

Conclusions

These test results confirm that stabilized hypochlorite solutions containing each of 5,5-dimethylhydantoin, benzenesulfonamide and succinimide, have antimicrobial effectiveness against K. pneumoniae at low total available chlorine (TAC) levels (e.g., 100 ppm TAC).

Example 5

Stability Studies

Materials and Methods

Preparation of a stock 3.0% stabilized hypochlorite solution (0.75 to 1.0 mole ratio of sulfamate to NaOCl, pH 4.9 citric acid buffer): Anhydrous citric acid (210.0 g), sulfamic acid (88.0 g) and sodium hydroxide (93.0 g) were dissolved in deionized water (1897.54 g). The reaction mixture was allowed to cool to room temperature (approximately 1 hour). Aqueous sodium hypochlorite (711.46 g of a 12.65% solution, 1.21 mol) was added slowly with stirring. The resulting solution, pH=4.9, was found to contain 3.0% stabilized NaOCl by iodometric titration.

All stabilized hypochlorite-containing test formulas were prepared by further dilution of the 3.0% stabilized NaOCl stock solution. Where applicable, the appropriate amount of each dopant was added to a known volume of diluted stock solution. Solutions containing varying mole ratios of sulfamate to NaOCl (1.0 to 1.0 and 1.5 to 1.0) were prepared by adding solid sodium sulfamate, as required, to 1.0 liter portions of the diluted stock solution. For all "doped" formulas, the ratio of NaOCl to dopant was 1.0:0.20.

Long-term stability samples were stored in a 40° C. incubator. After cooling to room temperature (23° C.) the concentration of NaOCl was determined via iodometric titration. The experimentally determined concentration of NaOCl is expressed in units of molarity (M). The recorded pH of each formula is shown in parentheses.

Stability Results at 40 Degrees Celsius

|  | Control-No Added dopant | 0.20/1.0 mol ratio 5,5-dimethylhydantoin/ NaOCl | 0.20/1.0 mol ratio benzenesulfonamide NaOCl |
|---|---|---|---|
| 0.75/1.0 mol ratio sulfamate/NaOCl | | | |
| Day 0 | 0.136M (5.09) | 0.136M (5.13) | 0.136M (5.10) |
| Day 21 | 0.121M (4.92) | 0.120M (4.94) | 0.121M (4.97) |
| Day 58 | 0.104M (4.91) | 0.103M (4.89) | 0.107M (4.89) |
| 1.0/1.0 mol ratio sulfamate/NaOCl | | | |
| Day 0 | 0.135M (5.09) | 0.135M (5.12) | 0.135M (5.09) |
| Day 21 | 0.120M (4.96) | 0.120M (4.96) | 0.123M (4.97) |
| Day 58 | 0.112M (4.91) | 0.111M (4.98) | 0.111M (4.91) |
| 1.5/1.0 mol ratio sulfamate/NaOCl | | | |
| Day 0 | 0.136M (5.08) | 0.136M (5.07) | 0.136M (5.07) |
| Day 21 | 0.124M (4.95) | 0.125M (4.96) | 0.124M (4.96) |
| Day 58 | 0.122M (4.93) | 0.119M (4.95) | 0.119M (4.92) |

Conclusions

The above results indicate that the addition of a dopant, such as 5,5-dimethylhydantoin or benzenesulfonamide, does not alter the long termn stability of hypochlorite solutions stabilized with sulfamate.

INDUSTRIAL APPLICABILITY

The present invention provides stabilized hypochlorite solutions having enhanced antimicrobial properties. The invention described herein is useful for a variety of cleaning applications where antimicrobial properties are desired. This includes "ready-to-use" cleaner applications, as well as compositions intended for dilution with additional water prior to use, such as a laundry sanitizer. We envision that this invention can also be used to control microorganisms in, for example, process streams and cooling towers. We also recognize that the solution can be used in other processes where an antimicrobial effect is required.

While the present invention has been described with respect to what is at present considered to be the preferred embodiments, it is to be understood that the invention is not limited to the disclosed embodiments. To the contrary, the present invention is intended to cover various modifications and equivalent arrangements included within the spirit and scope of the appended claims. The scope of the following claims is to be accorded the broadest interpretation so as to encompass all such modifications and equivalent formulations and functions.

We claim:

1. An antimicrobial solution comprising:
    a stabilized hypochlorite solution consisting essentially of a buffered aqueous combination of mono-N-chlorosulfamate ($HClNSO_3^-$) and di-N-chlorosulfamate ($Cl_2NSO_3^-$), the stabilized hypochlorite solution being prepared by mixing a source of hypochlorite and a source of sulfamate; and
    at least one dopant selected from the group consisting of a dialkyl hydantoin, an aryl sulfonamide, and a succinimide,
    wherein the concentration of total available chlorine present is about 100 to about 50,000 parts per million.

2. The solution of claim 1, wherein the dialkyl hydantoin is a 5,5-dialkyl hydantoin.

3. The solution of claim 1, wherein at least one dopant is present in a minor mole fraction in the solution, relative to the molar amount of stabilized hypochlorite present in the antimicrobial solution.

4. The solution of claim 2, wherein the 5,5-dialkyl hydantoin is selected from the group consisting of 5,5-dimethylhydantoin, 5-ethyl-5-methylhydantoin, and 5,5-diethylhydantoin.

5. The solution of claim 1, wherein the aryl sulfonamide is selected from the group consisting of benzene sulfonamide, toluene sulfonamide, 4-carboxybenzenesulfonamide, and a substituted derivative of any one of these compounds.

6. The solution of claim 1, wherein a buffer for the buffered aqueous combination is derived from an acid selected from the group consisting of citric acid, polyacrylic acid, acetic acid, propanoic acid, succinic acid, glutaric acid, adipic acid, boric acid, and phosphoric acid.

7. The solution of claim 1, wherein the solution has a pH between about 2 and about 10.

8. The solution of claim 1, wherein the solution has a pH between about 2 and about 7.

9. The solution of claim 1, wherein the solution has a pH between about 3 and 5 about 6.

10. The solution of claim 1, further comprising at least one of the ingredients selected from the group consisting of a surfactant, a chelating agent, a fragrance, a bromide-ion containing salt, a hypobromite source and a thickener.

11. The solution of claim 1, wherein the concentration of total available chlorine present is about 100 to about 20,000 parts per million.

12. The solution of claim 1, wherein the concentration of total available chlorine present is about 100 to about 10,000 parts per million.

13. A stabilized hypochlorite composition having enhanced microbial efficacy, and having a sulfamate to hypochlorite mole ratio of at least about 0.5:1.0, and a minimum mole ratio of dopant to hypochlorite of about 1:50, wherein the concentration of total available chlorine present is about 100 to about 50,000 parts per million, and wherein the dopant comprises at least one dopant selected from the group consisting of a dialkyl hydantoin, an aryl sulfonamide, and a succinimide.

14. The composition of claim 13, wherein the concentration of total available chlorine present in about 100 to about 20,000 parts per million.

15. The composition of claim 13, wherein the concentration of total available chlorine present is about 100 to about 10,000 parts per million.

16. An antimicrobial solution comprising:

a stabilized hypochlorite solution consisting essentially of a buffered aqueous combination of mono-N-chlorosulfamate ($HClNSO_3^-$) and di-N-chlorosulfamate ($Cl_2NSO_3^-$), the stabilized hypochlorite solution being prepared by mixing a source of hypochlorite and a source of sulfamate; and at least one dopant selected from the group consisting of toluenesulfonamide, benzenesulfonamide, succinimide, and dimethylhydantoin, wherein the concentration of total available chlorine present is about 100 to 2000 parts per million.

17. The solution of claim 16, wherein a buffer for the buffered aqueous combination is derived from an acid selected from the group consisting of citric acid, polyacrylic acid, acetic acid, propanoic acid, succinic acid, glutaric acid, adipic acid, boric acid, and phosphoric acid.

18. The solution of claim 16, wherein the solution has a pH between about 2 and about 10.

19. The solution of claim 16, wherein the solution has a pH between about 2 and about 7.

20. The solution of claim 16, wherein the solution has a pH between about 3 and about 6.

* * * * *

UNITED STATES PATENT AND TRADEMARK OFFICE
CERTIFICATE OF CORRECTION

PATENT NO.      : 6,471,974 B1                                      Page 1 of 1
DATED           : October 29, 2002
INVENTOR(S)     : Wayne M. Rees et al.

It is certified that error appears in the above-identified patent and that said Letters Patent is hereby corrected as shown below:

<u>Column 14,</u>
Line 67, "and 5" should read -- and --.

Signed and Sealed this

Seventh Day of October, 2003

JAMES E. ROGAN
*Director of the United States Patent and Trademark Office*